(12) United States Patent
Larkin et al.

(10) Patent No.: US 11,798,675 B2
(45) Date of Patent: Oct. 24, 2023

(54) GENERATING AND SEARCHING DATA STRUCTURES THAT FACILITATE MEASUREMENT-INFORMED TREATMENT RECOMMENDATION

(71) Applicant: Otsuka America Pharmaceutical Inc., Rockville, MD (US)

(72) Inventors: Roland Larkin, Rockville, MD (US); Srikanth Gottipati, Princeton Junction, NJ (US); Reza Moghadam, Yardley, PA (US); Carolyn Tyler, Victor, NY (US); Gregory Ho, South Brunswick, NJ (US)

(73) Assignee: OTSUKA AMERICA PHARMACEUTICAL, INC., Rockville, MD (US)

( * ) Notice: Subject to any disclaimer, the term of this patent is extended or adjusted under 35 U.S.C. 154(b) by 57 days.

(21) Appl. No.: 16/425,921

(22) Filed: May 29, 2019

(65) Prior Publication Data
US 2019/0371453 A1    Dec. 5, 2019

Related U.S. Application Data

(60) Provisional application No. 62/677,656, filed on May 29, 2018.

(51) Int. Cl.
*G16H 10/60* (2018.01)
*G16H 20/70* (2018.01)
(Continued)

(52) U.S. Cl.
CPC ........... *G16H 20/70* (2018.01); *A61B 5/0022* (2013.01); *G16H 10/60* (2018.01); *G16H 50/30* (2018.01)

(58) Field of Classification Search
CPC ........ G16H 20/70; G16H 10/60; G16H 50/30; G16H 40/67; G16H 50/20; A61B 5/0022
(Continued)

(56) References Cited

U.S. PATENT DOCUMENTS

| 2001/0023419 A1* | 9/2001 | Lapointe | G16H 50/20 706/15 |
| 2017/0323485 A1* | 11/2017 | Samec | A61B 3/113 |

(Continued)

FOREIGN PATENT DOCUMENTS

WO    WO 2017/106770    6/2017

OTHER PUBLICATIONS

Chekroud et al., "Cross-trial prediction of treatment outcome in depression: a machine learning approach," The Lancet Psychiatry, Jan. 2016, 3(3), 243-250.

(Continued)

*Primary Examiner* — Jonathan Ng
*Assistant Examiner* — Benjamin L. Hanks
(74) *Attorney, Agent, or Firm* — Pillsbury Winthrop Shaw Pittman LLP

(57) ABSTRACT

Methods, systems, apparatus, including computer programs encoded on computer storage media for generating psychiatric treatment recommendations. In one aspect, the method includes actions of receiving, by a server and from a first user device, one or more data structures that collectively include fields structuring data that represents (i) current patient symptoms and (ii) current patient diagnoses, generating, by the server, rendering data structure that includes
(Continued)

fields structuring data that represents rendering data that, when rendered on a display device, presents a patient dashboard based on the data that is received from the mobile device, and providing, by the server, the rendering data structure to a second user device that is different than the first user device, wherein the second user device is configured to render the rendering data structured by the fields of the rendering data structure to output the patient dashboard on the display of the second user device.

20 Claims, 5 Drawing Sheets

(51) Int. Cl.
*G16H 50/30* (2018.01)
*A61B 5/00* (2006.01)

(58) Field of Classification Search
USPC ........................................... 705/2–3
See application file for complete search history.

(56) References Cited

U.S. PATENT DOCUMENTS

2018/0096740 A1* 4/2018 Moturu .................. G16H 15/00
2019/0019581 A1* 1/2019 Vaughan ................ G16H 50/20

OTHER PUBLICATIONS

Cohen, et al., "Treatment Selection in Depression," Annual Review of Clinical Psychology, May 2018, 14(1):209-236.

Khodayari-Rostamabad et al., (2011). "Using pre-treatment electroencephalography data to predict response to transcranial magnetic stimulation therapy for major depression," 2011 Annual International Conference of the IEEE Engineering in Medicine and Biology Society, Sep. 2011, 6418-6421.

PCT International Search Report and Written Opinion in International Appln. No. PCT/US2019/034475, dated Aug. 21, 2019, 21 pages.

* cited by examiner

300

```
┌─────────────────────────────────────────────────────────────┐
│  OBTAIN ONE OR MORE FIRST DATA STRUCTURES FROM A FIRST      │
│  DISTRIBUTED DATA SOURCE THAT EACH REPRESENT FIRST DATA     │
│       THAT INCLUDES (I) CURRENT PATIENT SYMPTOMS            │
│                                                         310 │
└─────────────────────────────────────────────────────────────┘
                              │
                              ▼
┌─────────────────────────────────────────────────────────────┐
│    OBTAIN ONE OR MORE SECOND DATA STRUCTURES FROM A         │
│   SECOND DISTRIBUTED DATA SOURCE THAT EACH REPRESENT        │
│   SECOND DATA THAT INCLUDES ONE OR MORE ELECTRONIC          │
│   MEDICAL RECORDS OR ONE OR MORE PATIENT NOTES      320     │
└─────────────────────────────────────────────────────────────┘
                              │
                              ▼
┌─────────────────────────────────────────────────────────────┐
│  OBTAIN ONE OR MORE THIRD DATA STRUCTURES FROM A THIRD      │
│   DISTRIBUTED DATA SOURCE THAT EACH REPRESENT THIRD         │
│  DATA THAT INCLUDES A TREATMENT RECOMMENDATION THAT         │
│             IS BASED ON THE FIRST DATA              330     │
└─────────────────────────────────────────────────────────────┘
                              │
                              ▼
┌─────────────────────────────────────────────────────────────┐
│ GENERATING A TRAINING DATA ITEM BY AN APPLICATION SERVER    │
│  USING ONE OR MORE OF THE FIRST DATA STRUCTURES, ONE OR     │
│ MORE OF THE SECOND DATA STRUCTURES, AND ONE OR MORE OF      │
│           THE THIRD DATA STRUCTURES                 340     │
└─────────────────────────────────────────────────────────────┘
```

OBTAIN ONE OR MORE DATA STRUCTURES THAT REPRESENT A LABELED TRAINING DATA ITEM, WHEREIN THE LABELED TRAINING DATA ITEM INCLUDES (I) TRAINING DATA REPRESENTING CURRENT PATIENT SYMPTOMS FROM A FIRST DISTRIBUTED DATA SOURCE AND CURRENT PATIENT DIAGNOSES FROM A SECOND DISTRIBUTED DATA SOURCE AND (II) A LABEL THAT SPECIFIES A RECOMMENDED TREATMENT FROM A THIRD DISTRIBUTED DATA SOURCE 410

SEARCH THE ONE OR MORE DATA STRUCTURES TO OBTAIN THE TRAINING DATA 420

PROVIDE THE TRAINING DATA AS AN INPUT TO A MACHINE LEARNING MODEL 430

OBTAIN AN OUTPUT THAT IS GENERATED BY THE MACHINE LEARNING MODEL BASED ON THE MACHINE LEARNING MODEL'S PROCESSING OF THE PROVIDED INPUT 440

SEARCH THE ONE OR MORE DATA STRUCTURES TO OBTAIN THE LABEL 450

DETERMINE A DIFFERENCE BETWEEN (I) THE LABEL FOR THE TRAINING DATA ITEM THAT INCLUDES THE RECOMMENDED TREATMENT FROM THE SECOND DISTRIBUTED DATA SOURCE AND (II) THE OUPTUT GENERATED BY THE MACHINE LEARNING MODEL 460

ADJUST ONE OR MORE PARAMETERS OF THE MACHINE LEARNING MODEL BASED ON THE DETERMINED DIFFERENCE BETWEEN (I) THE LABEL FOR THE TRAINING DATA ITEM THAT INCLUDES THE RECOMMENDED TREATMENT FROM THE SECOND DISTRIBUTED DATA SOURCES AND (II) THE OUTPUT GENERATED BY THE MACHINE LEARNING MODEL 470

FIG. 4

GENERATING AND SEARCHING DATA STRUCTURES THAT FACILITATE MEASUREMENT-INFORMED TREATMENT RECOMMENDATION

CROSS-REFERENCE TO RELATED APPLICATIONS

This application claims the benefit of U.S. Provisional Patent Application No. 62/677,656 filed May 29, 2018 and entitled "SEARCHING DATA STRUCTURES IN IMPLEMENTING MACHINE LEARNING MODELS FOR GENERATING RECOMMENDATIONS," which is incorporated herein by reference in its entirety.

BACKGROUND

Psychiatric treatment recommendations can typically be made based on a physician's determination of one or systems during an in-person evaluation by the physician during a physician appointment.

SUMMARY

Aspects of the present disclosure are directed towards measurement-informed system determination by one or more software application employed on a user device. The measurement-informed determinations can provide non-conventional methods of measuring one or more patient symptoms that can provide vital information to a machine learning model trained to generate patient recommendations. These provided measurement-informed leads to more accurate diagnoses, better treatment recommendations, and facilitates real-time updating of physician dashboard that enable real-time treatment recommendations to be generated and evaluated for a patient based on measurement-informed determinations that can be constantly generated, and provided to a cloud-based monitoring system, by the patient's user device.

According to one innovative aspect of the present disclosure, a method for generating psychiatric treatment recommendations. In one aspect, the method can include actions that includes obtaining, by a server of a cloud-based patient monitoring system and from a first user device, (i) one or more first data structures that include fields structuring data that represents measurement-informed information related to current patient symptoms and (ii) one or more second data structures that include fields structuring data that represents diagnoses for the patient, with each data structure further including keyed data that identifies a patient, correlating the one or more first data structures with the one or more second data structures based on the keyed data that identifies the patient, extracting data representing (i) the measurement-informed information related to current patient symptoms and (ii) the diagnoses for the patient from the one or more first data structures or the one or more second data structures, generating, by the server of the cloud-based patient monitoring system, an input data structure based on the extracted data, for input to a machine learning model that is trained to predict psychiatric treatment recommendations for a patient, obtaining, by the server of the cloud-based patient monitoring system, output data generated by the machine learning model based on the machine learning model's processing of the input data structure, generating, by the server of the cloud-based patient monitoring system, a rendering data structure that includes fields structuring data that represents rendering data, that when rendered by a user device, causes the user device to display a patient dashboard that displays a treatment recommendation for the patient based on the output data generated by the machine learning model, and providing, by the server of the cloud-based patient monitoring system, the rendering data structure to a second user device that is different than the first user device, wherein the second user device is configured to render the rendering data to output the patient dashboard on the display of the second user device.

Other versions include corresponding systems, apparatus, and computer programs to perform the actions of methods defined by instructions encoded on computer readable storage devices.

These and other versions may optionally include one or more of the following features. For instance, in some implementations, the measurement-informed information related to current patient symptoms is generated by a native application installed on the first user device that is configured to measure one or more characteristics of a user related to a psychiatric disorder.

In some implementations, the measurement-informed information related to the current patient system is generated based on inferences made by the first user device or the server of the cloud-based monitoring system based on data that describes user interaction with applications on the first user device.

In some implementations, the method can further include determining, by the server of the cloud-based patient monitoring system, whether the measured-informed information related to the current patient is indicative of one or more symptoms of a psychiatric disorder.

In some implementations, the diagnosis for the current patient symptoms is based on one or more electronic medical records.

In some implementations, method can further include obtaining, by the server of the cloud-based patient monitoring system, information, based on the measurement-informed information, that describes a potential treatment from a digest of treatments.

In some implementations, the method can further include generating, by the server of the cloud-based patient monitoring system, a training data item, for training the machine learning model, based on the (i) measurement-informed information, (ii) the diagnosis for the current patient symptoms, and (iii) the potential treatment from the digest.

In some implementations, the patient dashboard displays the measurement-informed information, one or more entity symptoms, one or more tools used to obtained the measurement-informed information, and one or more treatment recommendations.

These and other aspects of the present disclosure are discussed in more detail in the detailed description below with reference to the accompanying drawings.

BRIEF DESCRIPTION OF THE DRAWINGS

FIG. 3 is a flowchart for an example of a process for generating an input to a machine learning model trained to generate measurement-informed treatment recommendations.

FIG. 4 is a flowchart for an example of a process for training a machine learning model to generate measurement-informed treatment recommendations.

DETAILED DESCRIPTION

The present disclosure is directed towards a method, system, apparatus, and computer program for generating measurement-informed psychiatric treatment recommendations. In some implementations, a user device of a patient can have access to a toolbox of software applications that, when executed by one or more processors of the mobile device, are configured to generate one or more data structures structuring information that describes a measurement-informed description of characteristics of a patient that relate to symptoms of one or more psychiatric disorders. Each application of the toolbox can be of a particular type and be configured to measure one or more particular symptoms. Measurement-informed information determined by one or more of the applications of the toolbox can be provided to an application server as current patient symptom data. The application server can correlate the current patient symptom data with other information related to the patient to generate an input to a machine learning model. The machine learning model can generate a measurement-informed psychiatric treatment recommendation based on the measurement-informed inputs and provide the generated measurement-informed psychiatric treatment recommendation, as well as additional information related to the patient, to a medical service provider device. The medical service provider device can generate a digital patient dashboard that the provider can use to review the generated recommendation based on the measurement-informed inputs to determine appropriate treatment options for the patient.

Figure 1:
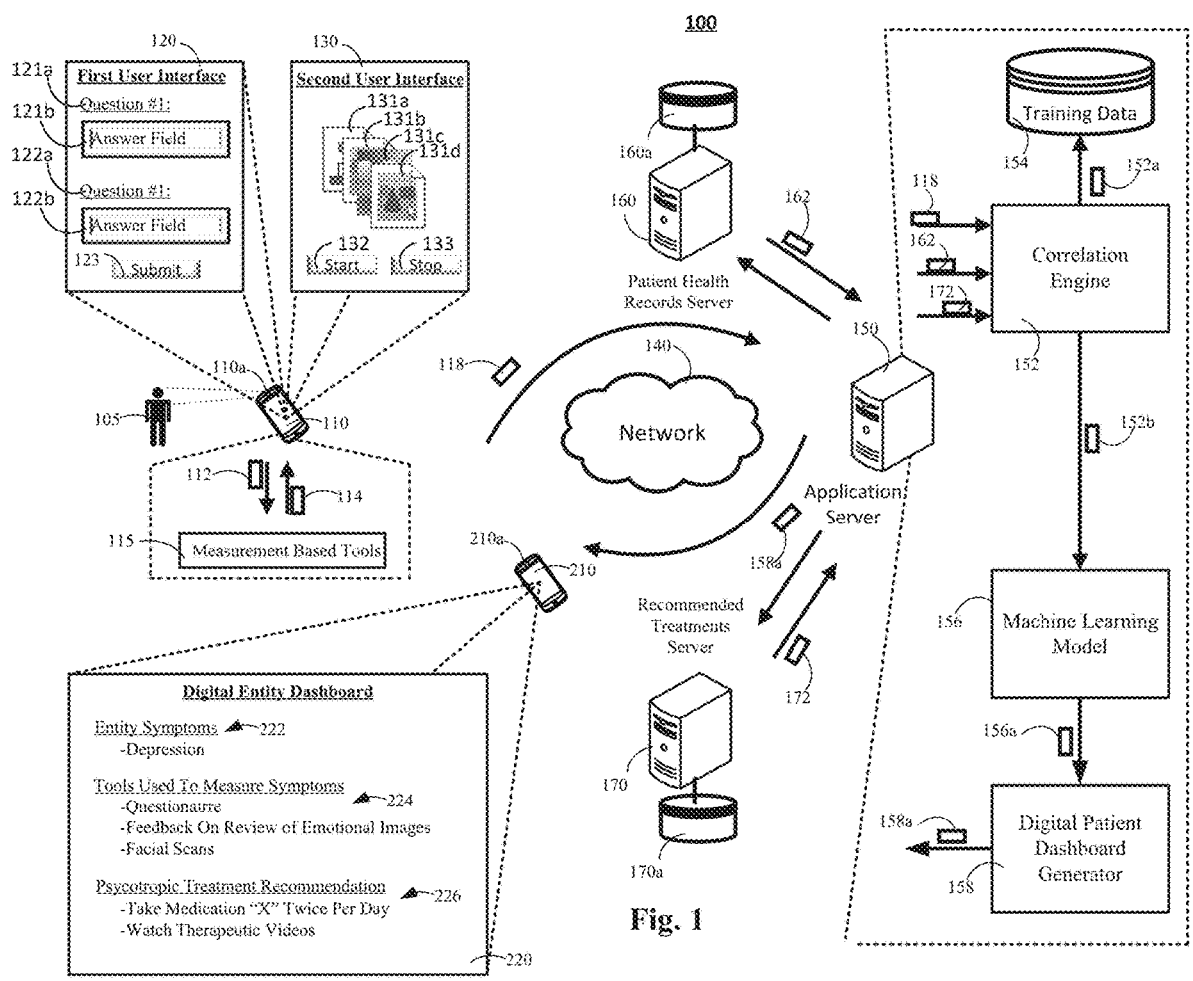
FIG. 1 is a contextual diagram for an example of a system for generating data structures for use in generating measurement-informed psychiatric treatment recommendations.

FIG. 1 is a contextual diagram for an example of a system 100 for generating data structures for use in generating measurement-informed psychiatric treatment recommendations. The system 100 can include a user device 110, one or more networks 140 an application server 150, a medical service provider device 210, and one or more information sources 160.

The user device 110 can include any client-side device used by a user to access measurement based tools. In some implementations the user device 110 can include a smartphone or a tablet device. In other implementations, the user device 110 can include a smartwatch, a laptop computer, a desktop computer, or the like. The user device 110 can include a variety of input and output devices, as known in the art. By way of example, the user device can include a camera 110a, a speaker, a display unit, and a microphone that enable input data to be captured from the user 105 and output data to be communicated to the user 105.

In some implementations, the user device 110 can store a toolbox 115 of measurement based tools on the user device 110. The toolbox 115 can include a library of software applications that, when executed, perform one or more operations configured to measure characteristics of a user 105 and determine whether the measured characteristic is indicative of one or more symptoms of a psychiatric medical conditions. Data structures can be generated by the software applications of the toolbox and provided to the application server 150, using the network 140, as a measurement-informed input to a correlation engine 153. The generated data structures can have fields that structure data describing measured characteristics determined by the particular application used to generate the data structure. The network 140 can include a local area network (LAN), a wide area network (WAN), a wireless network, an Ethernet network, an optical network, a cellular network, the Internet, or any combination thereof.

In some implementations, the measured-informed input provided to the correlation engine 153 of the application server 150 can include data a data structure having fields that structure data describing a single measured characteristic generated by a single application. In other implementations, the measured-informed input can be multiple data structures generated by one or more applications that each describe a different measured characteristic.

With reference to FIG. 1, a user 105 can submit a request 112 for access to a measurement based tool. In some implementations, the request 112 can be initiated by the user 105 as part of a randomly determined, self-evaluation that is initiated by the user 105. In other implementations, the request 112 may be initiated as part of a scheduled routine that was prescribed to the user 105 by a medical services provider such as a primary care physician, a psychologist, or the like. In some implementations, the request 112 can be an instruction from the user 105 that instructs the toolbox 115 of measurement based tool to launch a particular application from the toolbox 115 that is configured to measure a particular characteristic of the user 105. In other implementations, the request can be a general request that, when processed by the user device 110, causes the user device to launch an application of the toolbox to measure a characteristic of a user in a manner prescribed by the medical services provider. In response to the request 112, an application of the toolbox 115 can generate data 114 that, when processed by the user device 110, causes the user device 110 to begin executions of one or more processes to measure a characteristic of the user 105.

In some implementations, the generated data 114 can include rendering that, when rendered by the user device 110, causes the user device 110 to display one or more graphical user interfaces that are configured to guide a process that enables one or more particular user 105 characteristics to be measured. In other implementations, the generated data 114 can prompt a user to provide a subsequent input such as selection of a graphical icon that, when selected, triggers capturing of one or more images of the user's 105 face using the user device 110 for evaluation of the presence of one or more characteristics of symptoms of a psychiatric disorder.

In some implementations, the generated data 114 in response to the request 112 can trigger display of an interface 120 from a first application of the toolbox 115. In this example, the user interface 120 of the first application can be configured to present a questionnaire to the user 105 that includes a plurality of questions 121a, 122a that each call for a particular response or answer 121b, 122b. The user device 114 can, using one or more of the applications of the toolbox 115, measure one or more first characteristics of the user 105 based on the responses or answers 121b, 122b to the questions 121a, 122a. In some implementations, the responses or answers 121b, 122b to the questions 121a, 122a can be weighted, scaled, or the like in order to transform the responses or answers 121b, 122b into data that represents a measure of one or more characteristics of a psychiatric disorder. A data structure 118 can be generated, by the first application of the toolbox, that includes fields structuring data that describes the measure of the one or more characteristics. In some implementations, the generated data structure that represents the measured one or more first characteristics of the user 105 can be provided to the application server 150.

In other implementations, the generated data 114 in response to the request 112 can trigger display of an interface 130 from a second application of the toolbox. In this example, the user interface 120 of the second application can be configured to present a plurality of different types of visual stimuli, audio stimuli, or both, and evaluate user 105 feedback based on the user's interpretation of the visual stimuli, audio stimuli, or both. For example, in some implementations, the stimuli can include display of a series of one or more mages 131*a*, 131*b*, 131*c*, 131*d*. Second application can provide the user with options for interacting with the stimuli such as the ability to start 132 a presentation of stimuli, stop 133 a presentation of stimuli, rate presented stimuli, like a presented stimuli, dislike a presented stimuli, re-play a presented stimuli, pause a presented stimuli for further viewing, discard a present stimuli, save a presented stimuli, or the like. In such examples, the stimuli can include audio output by a speaker of a user device, images or videos displayed by the display of the user device, or the like. The second application can initially select the stimuli, from a library of stimuli randomly selected still images, videos, or the like. The second application can measure the user's 105 response to the present stimuli such as user interactions with stimuli and responses to stimuli.

In some implementations, the second application of the user device can use one or more microphones of the user device to detect and record data user feedback such as data describing the user's 105 breathing in response to the stimuli. In some implementations, user feedback information such as the user's 105 heart rate increases, decreases, and plateaus can be measured using a user device coupled to the user 105 such as a smartwatch. The second application can scale, score, or the like, the user feedback detected by the second application and generate one or more data structures that includes fields structuring the measured user feedback.

In some implementations, the measured user feedback can be weighted, scaled, or the like in order to transform the measured user feedback into data that represents a measure of one or more characteristics of a psychiatric disorder. The second application can generate a data structure 118 that includes fields structuring data that describes the measure of the one or more characteristics of the psychiatric order indicated by the user feedback. In some implementations, the generated data structure that represents the measured one or more first characteristics of the user 105 can be provided to the application server 150.

In other implementations, the generated data 114 in response to the request 112 can cause a third application of the toolbox 115 to capture one or more images of the user. For example, the generated data 114 can cause an application of a user device 110 to capture one or more facial images of the user 105 using the camera 110*a*. The third application can then analyze the captured one or more facial images to measure features of the face of the user 105 for indications of one or more symptoms of one or more psychiatric disorders. Data representing the measured features of the face of the user 105 can be weighted, scaled, or the like in order to transform the measured features of the face of the user 105 into data that represents a measure of one or more characteristics of a psychiatric disorder. The third application can generate a third data structure 118 that includes fields structuring data that describes the measure of the one or more characteristics of the psychiatric disorder indicated by the measured features of the face of the user.

The first application, second application, and third application described with reference to FIG. 1 are example of types of measuring tools that can be provided by the toolbox 115. However, the present disclosure need not be so limited. Instead, any type of application that is configured to measure a characteristic of a user can be used as an application of the toolbox 115. Such applications may be native applications installed on the user device 110 or web applications operating in a browsers. Such applications may operate in the foreground, operate in the background, or both.

For instance, in some implementations, measuring tools can be employed by the user device 110 that do not necessarily employ a particular test that is used to measure one or more particular characteristics of a user 105. Instead, the toolbox 115 of measurement based tools can employ one or more applications, processes, or the like that execute in the background of the user device and monitor the user's behavior. In such instances, the user device can generate measurement-informed information that measure characteristics of a user 105 such interaction with applications installed on the user device and determine, based on the user's 105 interaction with the application, whether the user 105 is exhibiting symptoms of one or more psychological disorders such as depression.

By way of example, in some implementations, the monitoring application can measure whether a user is exhibiting symptoms of one or more psychological disorders in a number of different ways. For example, in some implementations, the monitoring application can determine that the user is exhibiting symptoms of one or more psychological disorders based on the frequency with which the user 105 switches between applications, based on the types of applications the user 105 is accessing, based on the content the user 105 is viewing within an application, or the like. By way of example, the monitoring application can measure, based on sensors in the user device 110 such as one or more accelerometers, one or more gyroscopes, one or more cameras, or a combination thereof, that a user 105 is still staring at a display of the user device 110 after content being provided by an application has come to an end. Such blank staring at the display of a user device 110 can indicate that a user is exhibiting symptoms of one or more psychological disorders such as depression. In yet other examples, the monitoring application can determine that user 105 frequently changes from application to application without completing a task in any particular application. In such instances, the monitoring application can determine that the user may be exhibiting symptoms of a psychological disorder such as attention deficit disorder. The user device 110 can generate a data structure such as data structure 118 that includes fields that structure measurement-information that represents user interactions with one or more applications that are representative of one or more symptoms of a psychological disorder.

The one or more data structures 118 generated by the user device 110 can include fields structuring information that describes measurement-informed information such as a measure of one or more characteristics of a psychiatric disorder exhibited by a user 105. In some implementations, the one or more data structures 118 can structure measurement-informed information generated by a single application of the toolbox 115. Alternatively, the one or more data structures 118 can be used to structure measurement-informed information generated from multiple different applications of the toolbox 115. In some implementations, the data structure 118 can be used to structure measurement-informed information generated by an application operating in the foreground that is designed to prompt a user for input, interaction, or both, and then generate measurement-informed information describing one or more characteristics of a user that can be indicative of one or more symptoms of a psychological disorder. In other implementations, the data structure 118 can be used to structure measurement-informed information generated by an application that operates in the background to measure user behavior such as interactions with one or more applications of the user device, interactions with the user device itself, or both, to generate measurement-informed information describing one or more characteristics of a user that can be indicative of one or more symptoms of a psychological disorder. Foreground operating applications may be launched upon an express request from a user. Background operation applications may be launched at the express command of a user or by a command such as an instruction from a remote device operated by a physician (or employee, agent, or associate of the physician) with or without the user's knowledge. It may be advantageous for a remote user such as a physician (or employee, agent, or associate of the physician) to launch the background operating application so that the user 105 does not change behavior given knowledge that the background processes are monitoring the user's interactions. In other implementations, the user 105 can be required to approve background monitoring of the user's interactions with applications, the user device 110, or both, in an effort to protect the user's privacy. In addition to data describing the measurement-informed information, each of the one or more data structures can included keyed data that describes unique identifier for the user 105. The unique identifier for the user 105 can be used, by the application server 150, to associate other data records related to the user 105 with the one or more data structures 118.

An application programming interface executing on the application server 150 can obtain the one or more data structures 118. The application programming interface executing on the application server 150 can obtain the keyed unique identifier in the one or more data structures 118 and use the keyed unique identifier to obtain patient records associated with the user 105 from the patient records server 160. In some implementations, the application server 150 generate a query that includes the obtained unique identifier and transmit the query to the patient records server 160 via the network 140. The patient records server 160 can execute the query against one or more patient records server database 160a. The patient records stored in the patient records server database 160a can include electronic medical records, patient diagnoses made based on a previous doctor's visits, results of one or more previously administered diagnostic tests, or any combination thereof. The patient health records 162 that (i) are responsive to the query executed by the patient records server 160 and (ii) include electronic medical records related to the patient identified by the keyed data, patient diagnoses made by a physician based on a previous physician visit by the patient identified by the keyed data, results of one or more diagnostic tests previously administered to the patient identified by the keyed data, or the like can be returned to the application server 150 in response to the executed query.

The application server 150 can receive the patient health records 162 that are responsive to the query that includes the keyed data identifying a patient. The application server 150 can obtain information from (i) the one or more data structures 118, (ii) the received patient health records 162, or (iii) both, and use obtained information as search parameters in another query. The other query can be generated by the application server 150 and provided to a recommended treatments server 170. The recommended treatments server 170 can execute the other query against a database 170a of treatment recommendations. The recommended treatments server 170 generate a response to the query that includes one or more recommendations 272 for treating current patient symptoms, current patient diagnoses, or the like. In some implementations, the one or more recommendations can include recommendations obtained from one or more psychiatric texts that are established as a treatment for the current patient symptoms, the current patient diagnoses, or the like. The application server 150 can receive the one or more recommendations 172.

An application programming interface of the application server 150 provide the one or more data structures 118, the patient health records received from the patient records server 160, and the one or more treatment recommendations 172 as inputs to a correlation engine 152. The correlation engine can generate one or more data structures based on the inputs received from the application programming interface of the application server 150.

By way of example, the correlation engine 152 can be configured to generate a training data structure for use in training the machine learning model 156. Generation of the training data structure includes correlating the one or more data structures and the patient health records based on keyed data that identifies the current patient that is associated with both the one or more data structures 118 and the patient health records 162. In some implementations, instead of inputting all of the one or more data structures 118, in their entirety to the correlation engine, the application server 150 can extract the measurement-informed information such as a measure of one or more characteristics of a psychiatric disorder exhibited from the server and provide the extracted information to the correlation engine. In such instances, the extracted information and the patient health records can be correlated using the keyed data identifying the current patient. Once the training data structure is generated, the application server 140 can generate a label for the training data structure using the one or more treatment recommendations 172 received by the application server 150. The labeled training data item 152a can be stored in a database 154 of labeled training data items. The labeled training data items such as labeled training data item 152a can then be used to train the machine learning model 156 at some point in time after its creation.

The correlation engine 152 can also be used to generate input data structures to the machine learning model 156 that has been trained using training data items 154 stored in the database of training data items prior to the generation of training data item 152a. For example, the correlation engine 152 can generate an input data structure 152b that by correlating the one or more data structures 118 and the patient health records 162 based on keyed data that identifies the current patient 105 that is associated with both the one or more data structures 118 and the patient health records 162. In some implementations, instead of inputting all of the one or more data structures 118, in their entirety to the correlation engine, the application server 150 can extract the measurement-informed information such as a measure of one or more characteristics of a psychiatric disorder exhibited by the patient from the server and provide the extracted information to the correlation engine. In such implementations, the correlation engine 152 can generate an input data structure 152b that includes the information extracted from the one or more data structures 118 and the patient health records 162. The machine learning model 156 that has been trained using training data items 154 can generate output data that includes a recommended treatment 156a for a given input data structure processed by the machine learning model 156.

The generated recommendation 156a can be provided as an input to a digital patient dashboard generator 158. The digital patient dashboard generator 158 can generate rendering data 158a that, when rendered by a user device, causes the user device to display a digital patient dashboard 220. Generating rendering data for the digital patient dashboard can include, for example identifying information associated with keyed data identifying the patient that was used to generate the input data structure to the machine learning model 156. The identified information can include the measurement-informed information such as a measure of one or more characteristics of a psychiatric disorder exhibited by the patient identified by keyed data, an identification of the one or more application tools from the toolbox 115 used to generate the measurement-informed information, a diagnoses for the patient identified by the patient identified by the keyed data, the one or more treatment recommendations 156a output by the machine learning model based on the machine learning model's processing of the input data structure 152b.

The application server 150 can provide the generated rendering data to a user device 210 of physician. The user device 210 is configured to render the render data 158a, which causes a display of the user device 210 to output the digital patient dashboard 220 in a display of the user device 210. The user device 210 can include, for example, a smartphone, tablet, smartwatch, laptop, desktop, or the like. The rendered digital patient health dashboard 220 can include multiple different types of information that a physician can evaluate to determine one or more treatments for the user 140. In some implementations, the different types of information can include entity symptoms 222, tools used to measure symptoms 224, psychotropic treatment recommendations 226, or the like. In some implementations, the symptoms 222 can include symptoms derived from measurement-informed information generated by a user device 110. In some implementations, the psychotropic treatment recommendations can include whether or not the patient (e.g., user 105) should be prescribed a medication, whether or not a patient's (e.g., user's 105) medication should be switched to a different medication or a different dosage, whether or not the patient (e.g., user 105) should participate in psychotherapy, or any combination thereof.

Figure 2:
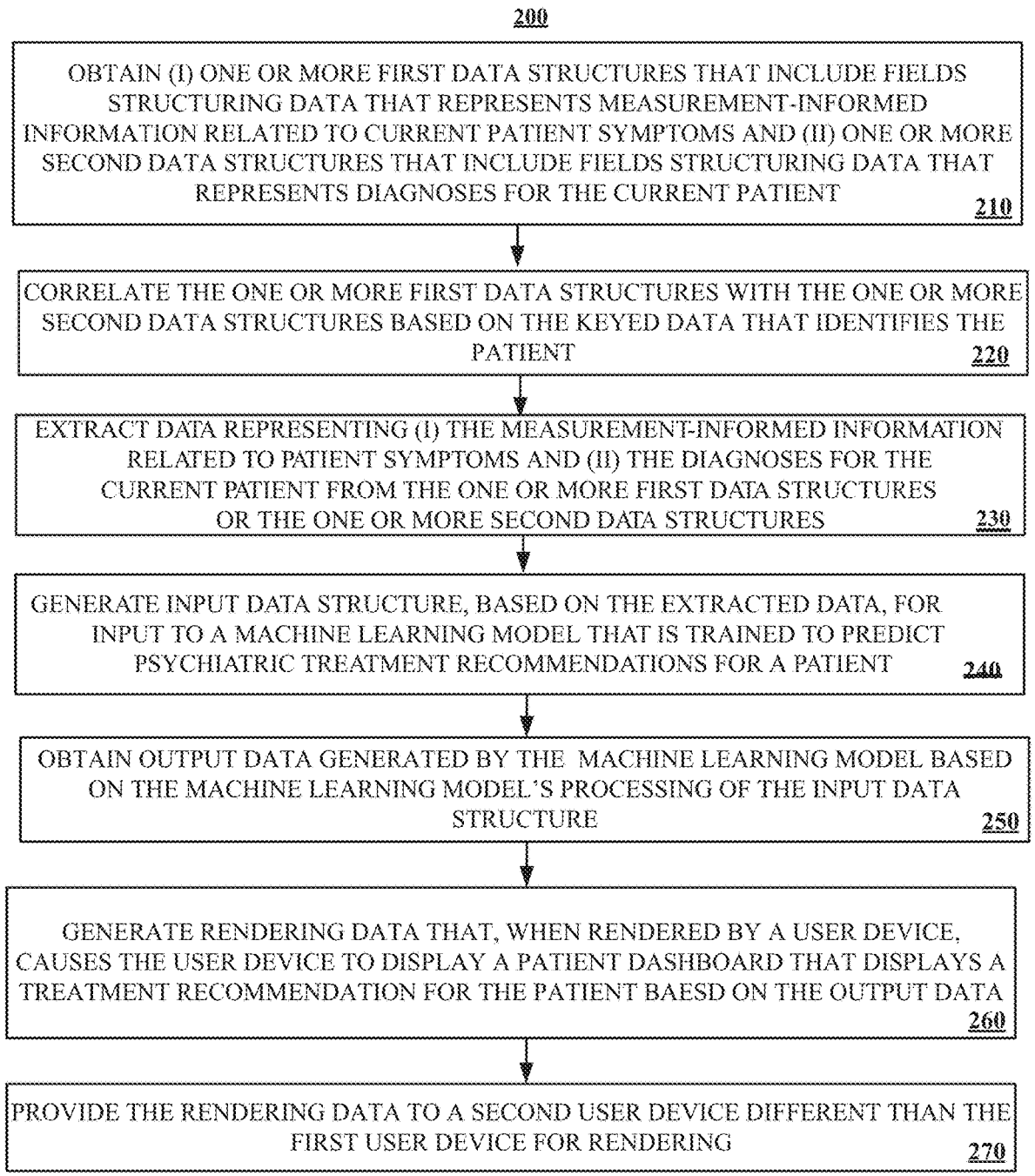
FIG. 2 is a flowchart for an example of a process for generating a patient treatment dashboard that provides measurement-informed psychiatric treatment recommendations.

FIG. 2 is a flowchart for an example of a process 200 of generating a patient treatment dashboard that provide measurement-informed psychiatric treatment recommendations. A computer system such as the computer system 100 of FIG. 1 can begin execution of process 200 by obtaining (I) one or more first data structures that includes fields structuring data that represents measurement-informed information related to a current patient's symptoms and (II) one or more second data structures that include fields structuring data that represents diagnoses for the patient (210). Measurement-informed information can include a description of characteristics of a patient that relate to symptoms of one or more psychiatric disorders. Diagnoses for the patient can include a diagnoses given, by a physician, in relation to a previous visit between the user or patient and the physician. In some implementations, the one or more first data structures and the one or more second data structures can be obtained from different distributed data sources. In other implementations, the one or more first data structures and the one or more second data structures can be obtained from the same data sources.

The computer system can continue execution of process 200 by correlating the one or more first data structures with the one or more second data structures based on the keyed data that identifies the patient (220). Correlating the one or more first data structures with the one or more second data structures based on the keyed data can include clustering the one or more first data structures and the one or more second data structures that have the same keyed data identifying a particular patient.

The computer system can continue execution or process 200 by extracting data representing (I) the measurement-informed information related to current patient symptoms and (II) the diagnoses for the patient from the one or more first data structures or the one or more second data structures (230). The computer system can generate an input data structure, based on the extracted data, for input to a machine learning model that is trained to predict psychiatric treatment recommendations for a patient (240). The computer system can obtain output data generated by the machine learning model based on the machine learning model's processing of the input data structure (250). The computer system can generate rendering data that, when rendered by a user device, causes the user device to display a patient dashboard that display a treatment recommendation for the patient based on the output data (260). The computer system can provide the rendering data to a second user device different than the first user device for rendering (270).

FIG. 3 is a flowchart for an example of a process 300 for generating an input to a machine learning model trained to generate measurement-informed treatment recommendations. A computer system such as the computer system of FIG. 1 can be used to execute the process 300. The computer system can begin execution of the process 300 by obtaining one or more first data structures from a first distributed data source that each represent first data that includes current patient symptoms (310). The first data that includes current patient symptoms can include measurement-informed information. Measurement-informed information can include a description of characteristics of a patient that relate to symptoms of one or more psychiatric disorders.

The computer system can continue execution of the process 300 by obtaining one or more second data structures from a second distributed data source that each represent second data that includes one or more electronic medical records or patient notes (320). The electronic medical records, patient notes, or both, can include data describing one or more diagnoses for the patient. Diagnoses for the patient can include a diagnoses given, by a physician, in relation to a previous visit between the user or patient and the physician.

The computer system can continue execution of the process 300 by obtaining one or more third data structures from a third distributed data source that each represent third data that includes a treatment recommendation that is based on the first data (330). Treatment recommendations can include peer-reviewed, government agency approved, or otherwise accepted, treatments for treating the one or more symptoms currently exhibited by the patient's symptoms, symptoms associated with a diagnoses for the patient, or both. The computer system can continue execution of the process 300 by generating a training data item by an application server using one or more of the first data structures, one or more of the second data structures, and one or more of the third data structures (340).

The generated training data item can include training data and a label. The training data can include the obtained data from the first distributed data source at stage 310 and the second distributed data source at stage 320. The data obtained from the third distributed data source can be used to generate a label for the generated training data item. The labeled training data item can be used to train a machine learning model to generate treatment recommendations based on measurement-informed information being received as an input to the machine learning model.

FIG. 4 is a flowchart for an example of a process 400 for training a machine learning model to generate measurement-informed treatment recommendations. A computer system such as the computer system 100 of FIG. 1 can be used to perform execution of the process 400. The computer system can begin execution of the process 400 by obtaining one or more data structures that represent a labeled training data item, wherein the labeled training data item includes (I) training data representing current patient symptoms from first distributed data source and a patient diagnoses from a second distributed data source and (II) a label that specifies a recommended treatment from a third distributed data source (410). In some implementations, the current patient symptoms can include measurement-informed information. Measurement-informed information can include a description of characteristics of a patient that relate to symptoms of one or more psychiatric disorders. In some implementations, the patient diagnoses can include a diagnoses given, by a physician, in relation to a previous visit between the user or patient and the physician. In some implementations, the recommended treatment can include peer-reviewed, government agency approved, or otherwise accepted, treatments for treating the one or more symptoms currently exhibited by the patient's symptoms, symptoms associated with a diagnoses for the patient, or both.

The computer system can continue execution of the process 400 by searching one or more data structures to obtain the training data (420). The computer system can continue execution of the process 400 by providing the training data as an input to a machine learning model (430). The computer system can continue execution of the process 400 by obtaining an output that is generated by the machine learning model based on the machine learning model's processing of the provided input (440). The computer system can continue execution of the process 400 by searching the one or more data structures to obtain the label (450). The computer system can continue execution of the process 400 by determining a difference between (I) the label for the training data item that includes the recommended treatment from the second distributed data source and (II) the output generated by the machine learning model (460). The computer system can continue execution of the process 400 by adjusting one or more parameters of the machine learning model based on the determined difference between (I) the label for the training data item that includes the recommended treatment from the second distributed data sources and (II) the output generated by the machine learning model (470).

Figure 5:
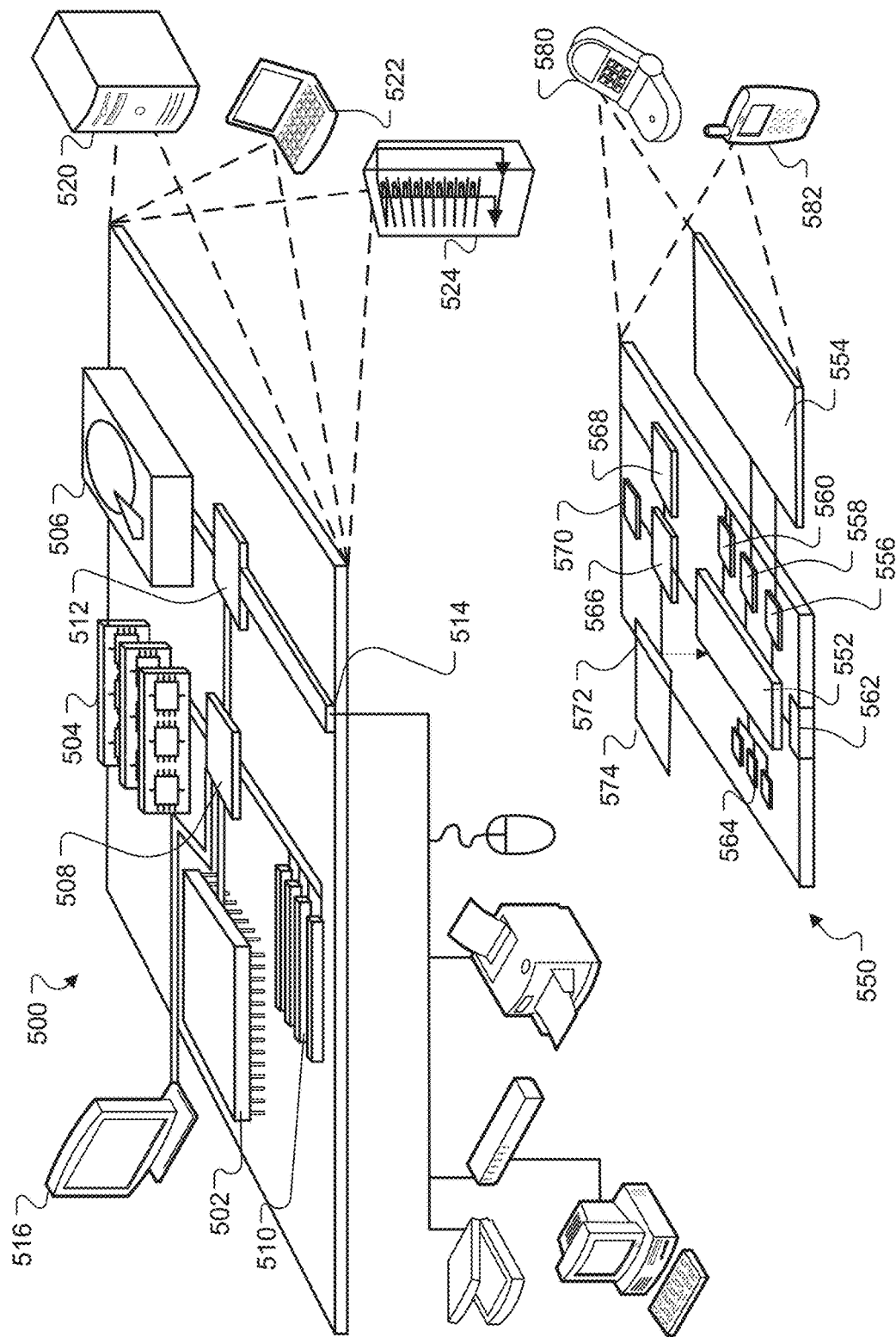
FIG. 5 is a diagram of computer system components that can be used to implement a system for generating data structures for use in generating measurement-informed psychiatric treatment recommendations.

FIG. 5 is a diagram of computer system 500 components that can be used to implement a system for generating data structures for use in generating measurement-informed psychiatric treatment recommendations.

Computing device 500 is intended to represent various forms of digital computers, such as laptops, desktops, workstations, personal digital assistants, servers, blade servers, mainframes, and other appropriate computers. Computing device 550 is intended to represent various forms of mobile devices, such as personal digital assistants, cellular telephones, smartphones, and other similar computing devices. Additionally, computing device 500 or 550 can include Universal Serial Bus (USB) flash drives. The USB flash drives can store operating systems and other applications. The USB flash drives can include input/output components, such as a wireless transmitter or USB connector that can be inserted into a USB port of another computing device. The components shown here, their connections and relationships, and their functions, are meant to be examples only, and are not meant to limit implementations of the inventions described and/or claimed in this document.

Computing device 500 includes a processor 502, memory 504, a storage device 508, a high-speed interface 508 connecting to memory 504 and high-speed expansion ports 510, and a low speed interface 512 connecting to low speed bus 514 and storage device 508. Each of the components 502, 504, 508, 508, 510, and 512, are interconnected using various busses, and can be mounted on a common motherboard or in other manners as appropriate. The processor 502 can process instructions for execution within the computing device 500, including instructions stored in the memory 504 or on the storage device 508 to display graphical information for a GUI on an external input/output device, such as display 516 coupled to high speed interface 508. In other implementations, multiple processors and/or multiple buses can be used, as appropriate, along with multiple memories and types of memory. Also, multiple computing devices 500 can be connected, with each device providing portions of the necessary operations, e.g., as a server bank, a group of blade servers, or a multi-processor system.

The memory 504 stores information within the computing device 500. In one implementation, the memory 504 is a volatile memory unit or units. In another implementation, the memory 504 is a non-volatile memory unit or units. The memory 504 can also be another form of computer-readable medium, such as a magnetic or optical disk.

The storage device 508 is capable of providing mass storage for the computing device 500. In one implementation, the storage device 508 can be or contain a computer-readable medium, such as a floppy disk device, a hard disk device, an optical disk device, or a tape device, a flash memory or other similar solid-state memory device, or an array of devices, including devices in a storage area network or other configurations. A computer program product can be tangibly embodied in an information carrier. The computer program product can also contain instructions that, when executed, perform one or more methods, such as those described above. The information carrier is a computer- or machine-readable medium, such as the memory 504, the storage device 508, or memory on processor 502.

The high-speed controller 508 manages bandwidth-intensive operations for the computing device 500, while the low speed controller 512 manages lower bandwidth intensive operations. Such allocation of functions is only an example. In one implementation, the high-speed controller 508 is coupled to memory 504, display 516, e.g., through a graphics processor or accelerator, and to high-speed expansion ports 510, which can accept various expansion cards (not shown). In the implementation, low-speed controller 512 is coupled to storage device 508 and low-speed expansion port 514. The low-speed expansion port, which can include various communication ports, e.g., USB, Bluetooth, Ethernet, wireless Ethernet can be coupled to one or more input/output devices, such as a keyboard, a pointing device, microphone/speaker pair, a scanner, or a networking device such as a switch or router, e.g., through a network adapter.

The computing device 500 can be implemented in a number of different forms, as shown in the figure. For example, it can be implemented as a standard server 520, or multiple times in a group of such servers. It can also be implemented as part of a rack server system 524. In addition, it can be implemented in a personal computer such as a laptop computer 522. Alternatively, components from computing device 500 can be combined with other components in a mobile device (not shown), such as device 550. Each of such devices can contain one or more of computing device 500, 550, and an entire system can be made up of multiple computing devices 500, 550 communicating with each other.

The computing device 500 can be implemented in a number of different forms, as shown in the figure. For example, it can be implemented as a standard server 520, or multiple times in a group of such servers. It can also be implemented as part of a rack server system 524. In addition, it can be implemented in a personal computer such as a laptop computer 522. Alternatively, components from computing device 500 can be combined with other components in a mobile device (not shown), such as device 550. Each of such devices can contain one or more of computing device 500, 550, and an entire system can be made up of multiple computing devices 500, 550 communicating with each other.

Computing device 550 includes a processor 552, memory 564, and an input/output device such as a display 554, a communication interface 566, and a transceiver 568, among other components. The device 550 can also be provided with a storage device, such as a micro-drive or other device, to provide additional storage. Each of the components 550, 552, 564, 554, 566, and 568, are interconnected using various buses, and several of the components can be mounted on a common motherboard or in other manners as appropriate.

The processor 552 can execute instructions within the computing device 550, including instructions stored in the memory 564. The processor can be implemented as a chipset of chips that include separate and multiple analog and digital processors. Additionally, the processor can be implemented using any of a number of architectures. For example, the processor 510 can be a CISC (Complex Instruction Set Computers) processor, a RISC (Reduced Instruction Set Computer) processor, or a MISC (Minimal Instruction Set Computer) processor. The processor can provide, for example, for coordination of the other components of the device 550, such as control of user interfaces, applications run by device 550, and wireless communication by device 550.

Processor 552 can communicate with a user through control interface 558 and display interface 556 coupled to a display 554. The display 554 can be, for example, a TFT (Thin-Film-Transistor Liquid Crystal Display) display or an OLED (Organic Light Emitting Diode) display, or other appropriate display technology. The display interface 556 can comprise appropriate circuitry for driving the display 554 to present graphical and other information to a user. The control interface 558 can receive commands from a user and convert them for submission to the processor 552. In addition, an external interface 562 can be provided in communication with processor 552, so as to enable near area communication of device 550 with other devices. External interface 562 can provide, for example, for wired communication in some implementations, or for wireless communication in other implementations, and multiple interfaces can also be used.

The memory 564 stores information within the computing device 550. The memory 564 can be implemented as one or more of a computer-readable medium or media, a volatile memory unit or units, or a non-volatile memory unit or units. Expansion memory 574 can also be provided and connected to device 550 through expansion interface 572, which can include, for example, a SIMM (Single In Line Memory Module) card interface. Such expansion memory 574 can provide extra storage space for device 550, or can also store applications or other information for device 550. Specifically, expansion memory 574 can include instructions to carry out or supplement the processes described above, and can also include secure information. Thus, for example, expansion memory 574 can be provided as a security module for device 550, and can be programmed with instructions that permit secure use of device 550. In addition, secure applications can be provided via the SIMM cards, along with additional information, such as placing identifying information on the SIMM card in a non-hackable manner.

The memory can include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 564, expansion memory 574, or memory on processor 552 that can be received, for example, over transceiver 568 or external interface 562.

Device 550 can communicate wirelessly through communication interface 566, which can include digital signal processing circuitry where necessary. Communication interface 566 can provide for communications under various modes or protocols, such as GSM voice calls, SMS, EMS, or MMS messaging, CDMA, TDMA, PDC, WCDMA, CDMA2000, or GPRS, among others. Such communication can occur, for example, through radio-frequency transceiver 568. In addition, short-range communication can occur, such as using a Bluetooth, Wi-Fi, or other such transceiver (not shown). In addition, GPS (Global Positioning System) receiver module 570 can provide additional navigation- and location-related wireless data to device 550, which can be used as appropriate by applications running on device 550.

Device 550 can also communicate audibly using audio codec 560, which can receive spoken information from a user and convert it to usable digital information. Audio codec 560 can likewise generate audible sound for a user, such as through a speaker, e.g., in a handset of device 550. Such sound can include sound from voice telephone calls, can include recorded sound, e.g., voice messages, music files, etc. and can also include sound generated by applications operating on device 550.

The computing device 550 can be implemented in a number of different forms, as shown in the figure. For example, it can be implemented as a cellular telephone 580. It can also be implemented as part of a smartphone 582, personal digital assistant, or other similar mobile device.

Various implementations of the systems and methods described here can be realized in digital electronic circuitry, integrated circuitry, specially designed ASICs (application specific integrated circuits), computer hardware, firmware, software, and/or combinations of such implementations. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor for displaying information to the user and a keyboard and a pointing device, e.g., a mouse or a trackball by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the systems and techniques described here, or any combination of such back end, middleware, or front end components. The components of the system can be interconnected by any form or medium of digital data communication, e.g., a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

Other Embodiments

A number of embodiments have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

The invention claimed is:

1. A computer-implemented method for generating measurement-informed psychiatric treatment recommendations for a user, the method comprising:
   providing, by one or more processing devices, a plurality of visual stimuli for output on a display of a first user device associated with a user;
   accessing, by the one or more processing devices, one or more first data structures, generated by the first user device, that include first keyed data identifying the user and a first field structuring data that represents a measurement of the user, the measurement representing a response of the user to the presentation of the plurality of visual stimuli;
   accessing, by the one or more processing devices, one or more second data structures that include second keyed data identifying the user and a second field structuring data that represents a diagnosis for the user by a medical professional;
   identifying, by the one or more processing devices, the first keyed data in the one or more first data structures and the second key data in the one or more second data structures;
   correlating, by the one or more processing devices, the one or more first data structures with the one or more second data structures based on the first keyed data and the second key data;
   extracting, by the one or more processing devices, from the correlated data, data representing (i) the measurement of the user from the one or more first data structures and (ii) the diagnosis for the user from the one or more second data structures;
   generating, by the one or more processing devices, an input data structure based on the extracted data representing (i) the measurement of the user from the one or more first data structures and (ii) the diagnosis for the user from the one or more second data structures, for input to a machine learning model that outputs one or more psychiatric treatment recommendations for the user;
   wherein the machine learning model is trained based on a training data item comprising training data and a label for the training data item, the label indicating a selection of the one or more psychiatric treatment recommendations that are each used as a label for the training data item and the training data comprising measurements of users and corresponding diagnoses of the users to learn associations between the measurements of users and the diagnoses to the one or more psychiatric treatment recommendations of the labeled training data item so that the one or more psychiatric treatment recommendations that are output by the machine learning model are based on the learned associations between measurements and the corresponding diagnoses to the one or more psychiatric treatment recommendations;
   obtaining, by the one or more processing devices, output data generated by the machine learning model based on the machine learning model's processing of the input data structure;
   determining, by the one or more processing devices, a treatment recommendation for the user based on the output data generated by the machine learning model;
   generating, by the one or more processing devices, a rendering data structure that includes fields structuring data that represents rendering data that, when rendered by a user device, causes the user device to display a dashboard that displays the treatment recommendation for the user based on the output data generated by the machine learning model; and providing, by the one or more processing devices, the rendering data structure to a second user device that is different than the first user device, wherein the second user device is configured to render the rendering data to output the dashboard on the display of the second user device.

2. The method of claim 1, wherein the diagnosis is based on one or more electronic medical records of the user, and wherein a second user of the second device is a physician.

3. The method of claim 1, the method further comprising: obtaining, based on the one or more first data structures, information indicative of a potential treatment.

4. The method of claim 3, the method further comprising: generating a training data item, for training the machine learning model, based on the first data structures, the second data structures and information indicative of the potential treatment.

5. The method of claim 1, wherein the dashboard displays the information indicative of the measurement of the user one or more software applications used to obtain the information indicative of the measurement of the user, and one or more treatment recommendations.

6. The method of claim 1, wherein the plurality of visual stimuli include a sequence of images displayed on the first user device.

7. The method of claim 1, the method further comprising: obtaining data representing a user biometric response to the plurality of visual stimuli, wherein the measurement is based on the obtained data.

8. The method of claim 1, further comprising:
generating labeled training data for the machine learning model, the labeled training data comprising: a label indicating a treatment option from among a digest of treatments and corresponding measurement of users and diagnoses of the users that received the treatment option; and
training the machine learning model based on the labeled training data to correlate the corresponding measurements of the users and the diagnoses of the users with the treatment option from among the digest of treatments.

9. The method of claim 1, wherein the measurement is made by a first application executing on the first user device, the method further comprising:
causing a second application executing on the first user device to collect a facial image of the user, wherein the facial image is used for training the machine learning model.

10. The method of claim 9, further comprising:
receiving, from the second device, a request to monitor activities of the user on the first user device; and
transmitting an instruction to the user device to execute a third application monitors the activities and generates one or more measurements based on the monitored activities, wherein the monitored activities are used for training the machine learning model.

11. A system for generating measurement-informed psychiatric treatment recommendations for a user comprising:
one or more computers and one or more storage devices storing instructions that are operable, when executed by the one or more computers, to cause the one or more computers to:
provide a plurality of visual stimuli for output on a display of a first user device associated with a user;

access one or more first data structures, generated by the first user device, that include first keyed data identifying the user and a first field structuring data that represents a measurement of the user, the measurement representing a response of the user to the presentation of the plurality of visual stimuli;

access one or more second data structures that include second keyed data identifying the user and a second field structuring data that represents a diagnosis for the user by a medical professional;

identify the first keyed data in the one or more first data structures and the second key data in the one or more second data structures;

correlate the one or more first data structures with the one or more second data structures based on the first keyed data and the second key data;

extract, from the correlated data, data representing (i) the measurement of the user from the one or more first data structures and (ii) the diagnosis for the user from the one or more second data structures;

generate an input data structure based on the extracted data representing (i) the measurement of the user and (ii) the diagnosis for the user from the one or more second data structures, for input to a machine learning model that outputs one or more psychiatric treatment recommendations for the user;

wherein the machine learning model is trained based on a training data item comprising training data and a label for the training data item, the label indicating a selection of the one or more psychiatric treatment recommendations that are each used as a label for the training data item and the training data comprising measurements of users and corresponding diagnoses of the users to learn associations between the measurements of users and the diagnoses to the one or more psychiatric treatment recommendations of the labeled training data item so that the one or more psychiatric treatment recommendations that are output by the machine learning model are based on the learned associations between measurements and the corresponding diagnoses to the one or more psychiatric treatment recommendations;

obtain output data generated by the machine learning model based on the machine learning model's processing of the input data structure;

determine a treatment recommendation for the user based on the output data generated by the machine learning model;

generate a rendering data structure that includes fields structuring data that represents rendering data that, when rendered by a user device, causes the user device to display a dashboard that displays the treatment recommendation for the user based on the output data generated by the machine learning model; and provide the rendering data structure to a second user device that is different than the first user device, wherein the second user device is configured to render the rendering data to output the dashboard on the display of the second user device.

12. The system of claim 11, wherein the diagnosis is based on one or more electronic medical records of the user, and wherein a second user of the second device is a physician.

13. The system of claim 11, wherein the instructions, when executed by the one or more computers, further cause the one or more computers to:
obtain, based on the first data structures information indicative of a potential treatment.

14. The system of claim 13, wherein the instructions, when executed by the one or more computers, further cause the one or more computers to:
generate, a training data item, for training the machine learning model, based on the first data structures, the second data structures, and information indicative of the potential treatment.

15. The system of claim 11, wherein the dashboard displays information indicative of the measurement of the user, one or more software applications used to obtain the information indicative of the measurement of the user, and one or more treatment recommendations.

16. A non-transitory computer-readable medium storing software comprising instructions executable by one or more computers which, upon such execution, cause the one or more computers to:
provide a plurality of visual stimuli for output on a display of a first user device associated with a user;
access one or more first data structures, generated by the first user device, that include first keyed data identifying the user and a first field structuring data that represents a measurement of the user, the measurement representing a response of the user to the presentation of the plurality of visual stimuli;
access one or more second data structures that include second keyed data identifying the user and a second field structuring data that represents a diagnosis for the user by a medical professional
identify the first keyed data in the one or more first data structures and the second key data in the one or more second data structures;
correlate the one or more first data structures with the one or more second data structures based on the first keyed data and the second key data;
extract, from the correlated data, data representing (i) the measurement of the user from the one or more first data structures and (ii) the diagnosis for the user from the one or more second data structures;
generate an input data structure based on the extracted data representing (i) the measurement of the user and (ii) the diagnosis for the user from the one or more second data structures, for input to a machine learning model that outputs one or more psychiatric treatment recommendations for the user;
wherein the machine learning model is trained based on a training data item comprising training data and a label for the training data item, the label indicating a selection of the one or more psychiatric treatment recommendations that are each used as a label for the training data item and the training data comprising measurements of users and corresponding diagnoses of the users to learn associations between the measurements of users and the diagnoses to the one or more psychiatric treatment recommendations of the labeled training data item so that the one or more psychiatric treatment recommendations that are output by the machine learning model are based on the learned associations between measurements and the corresponding diagnoses to the one or more psychiatric treatment recommendations;
obtain output data generated by the machine learning model based on the machine learning model's processing of the input data structure;
determine a treatment recommendation for the user based on the output generated by the machine learning model;
generate a rendering data structure that includes fields structuring data that represents rendering data that, when rendered by a user device, causes the user device to display a dashboard that displays the treatment recommendation for the user based on the output data generated by the machine learning model; and
provide the rendering data structure to a second user device that is different than the first user device, wherein the second user device is configured to render the rendering data to output the dashboard on the display of the second user device.

17. The computer readable medium of claim 16, wherein the diagnosis is based on one or more electronic medical records of the user, and wherein a second user of the second device is a physician.

18. The computer readable medium of claim 16, wherein the instructions, when executed by the one or more computers, further cause the one or more computers to:
obtaining, based on the first data structures, information indicative of a potential treatment.

19. The computer readable medium of claim 18, wherein the instructions, when executed by the one or more computers, further cause the one or more computers to:
generate a training data item, for training the machine learning model, based on the first data structures, the second data structures, and information indicative of the potential treatment.

20. The computer-readable medium of claim 16, wherein the dashboard displays information indicative of the measurement of the user, one or more software applications used to obtain the information indicative of the measurement of the user, and one or more treatment recommendations.

* * * * *